United States Patent [19]
Forman

[11] 4,390,014
[45] Jun. 28, 1983

[54] SELF-RETAINING RIB BELT
[76] Inventor: Everett W. Forman, 31 Harper St., Stamford, N.Y. 12167
[21] Appl. No.: 310,889
[22] Filed: Oct. 13, 1981
[51] Int. Cl.³ .............................................. A61F 5/02
[52] U.S. Cl. ........................................ 128/78; 2/338
[58] Field of Search ............ 128/78, DIG. 15; 2/338, 2/339

[56] References Cited
U.S. PATENT DOCUMENTS

| | | | |
|---|---|---|---|
| 2,723,664 | 11/1955 | Davis | 128/78 |
| 3,097,640 | 7/1963 | Morgan | 128/78 |
| 3,441,027 | 4/1969 | Lehman | 128/78 |
| 3,920,008 | 11/1975 | Lehman | 128/78 |

FOREIGN PATENT DOCUMENTS
1091052 10/1960 Fed. Rep. of Germany .......... 2/338

Primary Examiner—John D. Yasko

[57] ABSTRACT

A non-elastic rib belt with a superimposed attached elastic means fastened over a portion of the belt, the elastic being attached over a longer length of the belt than the length of the unstretched elastic. Thus, when applied to the chest, the non-elastic belt finitely restricts expansion during inhalation, while the contracting elastic takes up the slack in the belt during exhalation, thereby preventing the belt from slipping, thus obviating the need for shoulder straps.

1 Claim, 2 Drawing Figures

SELF-RETAINING RIB BELT

SUMMARY OF THE INVENTION

1. Field of the Invention

The present invention relates to rib belts, and specifically to a non-elastic rib belt with attached elastic members which obviate the need for shoulder straps.

2. Description of Prior Art

Heretofore pleurisy, minor rib fractures, intercostal sprains and strains frequently have been treated with circular bandages with closure means. These are generally referred to as "rib belts." These belts consist of two general types: one, a flexible non-elastic bandage with shoulder straps to prevent slippage; and two, a flexible bandage with elastic material either throughout or partially incorporated in the belt. In the second type shoulder straps are not essential since the elastic prevents slippage; however the elastic types do not prevent chest expansion beyond the finite critical level required in each particular case to prevent pain and consequent tissue damage.

Non-elastic rib belts, with shoulder straps, are shown in U.S. Pat. Nos. 2,662,522, 2,723,664 and 2,815,752. Rib belts, partly or completely incorporating elastic have been available commercially for many years. In addition clothing is available combining a non-elastic encircling portion with attached elastic material. A common example of this latter is in men's pants having a non-elastic waistband combined with an inner adjustable elastic. Functionally, however, this is the mechanical equivalent to the incorporation of an elastic element in the waistband itself since, with tension applied to the elastic element, there is created an inner circumference involving the elastic; however the full circumference of the non-elastic portion does not come into use since the abdomen does not rapidly expand and contract as does the thorax, or chest.

3. Object of the Invention

An object of the present invention is to provide a rib belt which will finitely restrict chest expansion during inhalation, yet, despite not having shoulder straps, will not slip during exhalation.

A further object is to reduce the constricting pressure on the chest throughout respiration as compared to belts with incorporated elastic in which the maintaining pressure is only slightly less than the not inconsiderable restricting pressure required for an effective splinting device.

A further object is to make the belt relatively inexpensive.

A further object is to provide for easy application and removal.

DETAILED DESCRIPTION OF THE INVENTION

Figure 1:
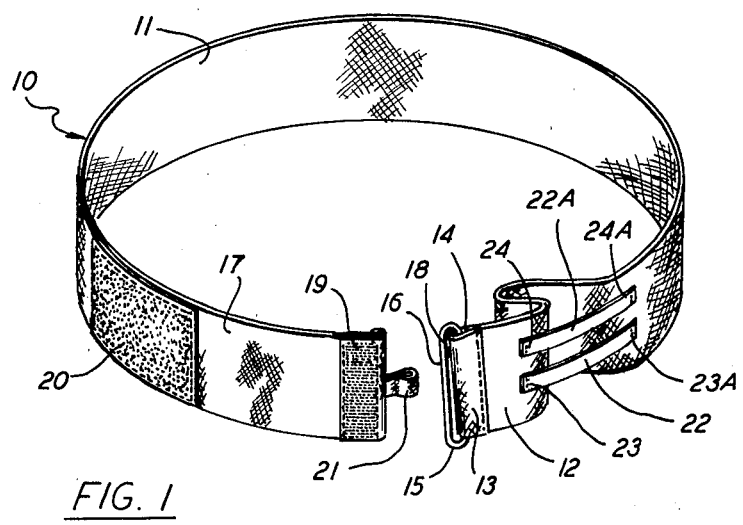
FIG. 1 is a perspective view of the belt partially applied, but without illustrating the patient.
Figure 2:
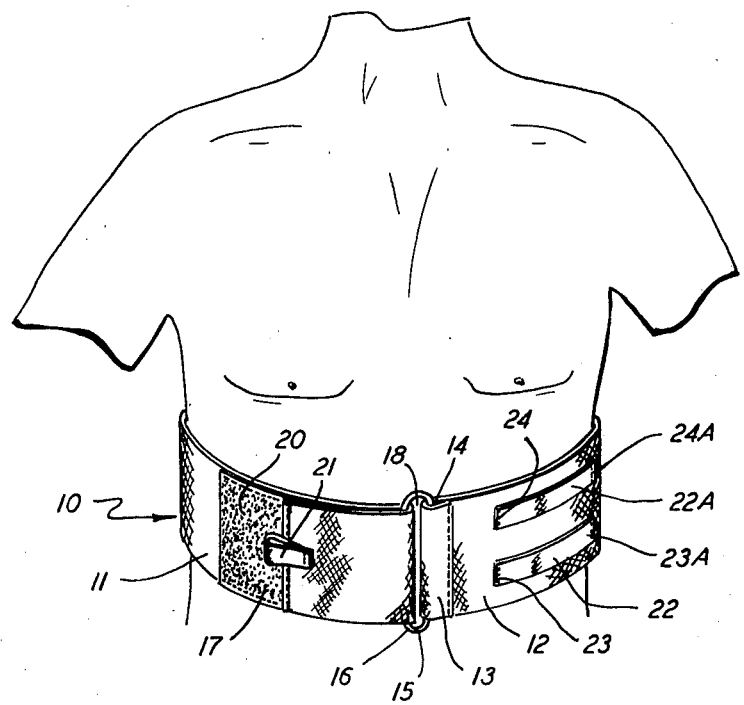
FIG. 2 is a perspective view of the belt applied, with the patient's chest expanded.

In both FIGS. 1 and 2 the rib belt 10 comprises the flexible elongate member 11 of bandage material, one end 12 of which has its terminal portion 13 reflected and attached to itself forming a loop 14. Loosely held in loop 14 is the closed substantially rectangular keeper 15 having the free bight portion 16 whose central opening 18 is longer than the width of member 11 so that the outer end portion 17 may be readily passed through the central opening of said keeper. Attached to the distal part of end portion 17 is an adherent means, in this case Velcro ™ hooks 19, and at an appropriate distance is affixed complementary adherent means 20, in this case Velcro ™ loops. Attached to the distal portion of outer end 17 is a tape loop 21. Two elastic tape members 22 and 22A are attached longitudinally to said elongate member 11 at their respective ends 23 and 23A and 24 and 24A in such manner that they overlap a longer longitudinal distance of the elongate member 11 than their own length.

In FIG. 1 there is slack in the elongate member 11 created by the restraining force of the two elastic tape members 22 and 22A. In FIG. 2 the elongate member 11 is stretched by inhalation and the two elastic tape members 22 and 22A are also in a stretched condition.

In use the rib belt 11 is placed around the chest, and the outer end 17 is passed behind the free bight portion 16 of the keeper 15 and through the central opening 18, then reflected back on itself. The adherent means 19 is then affixed to the complementary adherent means 20, tension being facilitated by a finger passed through the tape loop 21 and pulling outer end 17 farther form inner end 12. The desired tension, hence constriction of the chest, can be more readily obtained by exhalation by the wearer during application of the belt. When the belt 10 is so applied, inhalation will be finitely limited by the elongate member 11, as in FIG. 2. However, during exhalation, when slack develops in the elongate member 11, the elastic tape members 22 and 22A have sufficient tension to take up the slack as shown in FIG. 1, thus preventing slippage.

What is claimed is:

1. A self-retaining rib belt comprising the combination of a flexible non-elastic elongate member of bandage material with adjustable closure means and a longitudinally attached outer elastic means, said elastic means unstretched length being shorter than the adjacent longitudinal portion of said elongate member whereby for various sized chests the elongate member obtains finite restriction of chest expansion during inhalation yet the contracting elastic means prevents slippage of the belt when the chest diminishes in size during exhalation.

* * * * *